(12) United States Patent
Kim et al.

(10) Patent No.: US 12,253,859 B2
(45) Date of Patent: Mar. 18, 2025

(54) DISINFECTION ROBOT CAPABLE OF AUTONOMOUS DRIVING AND AUTOMATIC RECOGNITION OF DISINFECTION TARGETS

(71) Applicant: KOREA INSTITUTE OF SCIENCE AND TECHNOLOGY, Seoul (KR)

(72) Inventors: Kanggeon Kim, Seoul (KR); Jongsuk Choi, Seoul (KR); Woosub Lee, Seoul (KR); Jun-Sik Kim, Seoul (KR); Soonkyum Kim, Seoul (KR); Sona Kwak, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 598 days.

(21) Appl. No.: 17/369,466

(22) Filed: Jul. 7, 2021

(65) Prior Publication Data

US 2022/0253067 A1    Aug. 11, 2022

(30) Foreign Application Priority Data

Feb. 9, 2021  (KR) .................. 10-2021-0018077

(51) Int. Cl.
  *G05D 1/00*    (2024.01)
  *A61L 2/10*    (2006.01)
  *G01C 21/00*   (2006.01)

(52) U.S. Cl.
  CPC ............. *G05D 1/0248* (2013.01); *A61L 2/10* (2013.01); *G01C 21/383* (2020.08);
  (Continued)

(58) Field of Classification Search
  None
  See application file for complete search history.

(56) References Cited

U.S. PATENT DOCUMENTS 11,037,320 B1 *  6/2021  Ebrahimi Afrouzi ... G06T 7/521
2005/0022330 A1  2/2005  Park et al.
(Continued)

FOREIGN PATENT DOCUMENTS

KR      100478681 B1    3/2005
KR      10-1371038 B1   3/2014
(Continued)

*Primary Examiner* — Truc M Do
(74) *Attorney, Agent, or Firm* — Rabin & Berdo, P.C.

(57) ABSTRACT

Disclosed is a disinfection robot capable of autonomous driving and recognition of a disinfection target. The disinfection robot includes: a recognition unit configured to generate recognition information by recognizing a surrounding environment of the disinfection robot; a movement unit configured to move a position of the disinfection robot; a light source unit configured to emit a light of a predetermined wavelength area for disinfection; an injection unit configured to inject a fluid for disinfection; and a control unit configured to move the disinfection robot through the movement unit based on the recognition information, wherein the control unit is configured to identify a disinfection target from the recognition information and control at least one of the light source unit and the injection unit to perform disinfection to at least one of the surrounding environment of the disinfection robot and the disinfection target.

11 Claims, 10 Drawing Sheets

(52) U.S. Cl.
CPC ......... *G05D 1/0212* (2013.01); *G05D 1/0274* (2013.01); *A61L 2202/11* (2013.01); *A61L 2202/14* (2013.01); *A61L 2202/16* (2013.01)

(56) References Cited

U.S. PATENT DOCUMENTS

| | | | |
|---|---|---|---|
| 2014/0330452 A1* | 11/2014 | Stewart | B25J 19/02 |
| | | | 701/2 |
| 2015/0199487 A1* | 7/2015 | Grauds | A61L 2/10 |
| | | | 250/365 |
| 2016/0271803 A1* | 9/2016 | Stewart | B25J 11/0085 |
| 2017/0246329 A1* | 8/2017 | Lloyd | A61L 2/24 |
| 2020/0019180 A1 | 1/2020 | Chae | |
| 2020/0306399 A1* | 10/2020 | Markesbery | A01N 25/06 |
| 2020/0397936 A1* | 12/2020 | Deros | G05D 1/0221 |
| 2021/0089040 A1* | 3/2021 | Ebrahimi Afrouzi | |
| | | | G05D 1/0248 |
| 2021/0299295 A1* | 9/2021 | Rubaek | A61L 2/24 |
| 2022/0111105 A1* | 4/2022 | Pan | A61L 9/20 |

FOREIGN PATENT DOCUMENTS

| | | |
|---|---|---|
| KR | 10-1724447 B1 | 4/2017 |
| KR | 10-1724481 B1 | 4/2017 |
| KR | 1020170037749 A | 4/2017 |
| KR | 10-1987133 B1 | 6/2019 |
| KR | 10-2012550 B1 | 8/2019 |
| KR | 1020190096874 A | 8/2019 |
| KR | 10-2020-0092262 A | 8/2020 |
| KR | 10-2156511 B1 | 9/2020 |
| KR | 102189255 B1 | 12/2020 |

* cited by examiner

140

LIGHT
EMISSION

DISINFECTION ROBOT CAPABLE OF AUTONOMOUS DRIVING AND AUTOMATIC RECOGNITION OF DISINFECTION TARGETS

CROSS-REFERENCE TO RELATED APPLICATION

This application claims priority to Korean Patent Application No. 10-2021-0018077, filed on Feb. 9, 2021 and all the benefits accruing therefrom under 35 U.S.C. § 119, the contents of which in its entirety are herein incorporated by reference.

BACKGROUND

1. Field

This disclosure relates to a disinfection robot capable of autonomous driving and automatic recognition of disinfection targets. Specifically, the present disclosure relates to a disinfection robot, which may perform disinfection by autonomous driving and automatic recognition of disinfection targets so that indirect disinfection based on a light source and direct disinfection through disinfectant injection are performed simultaneously.

2. Description of the Related Art

With the outbreak of the COVID-19 virus, the interest in disinfection to prevent the spread of infectious diseases or disinfect the affected area is increasing around the world. However, the disinfection work up to now has been performed in such a way that a worker carries a disinfection device while moving the space required for disinfection. Accordingly, the worker could not be completely free from the risk of infection even if the worker wore a disinfection suit.

In addition, conventionally, a device placed in a certain place to inject a disinfectant periodically or through object recognition has been proposed, but such a device has a limitation that the disinfection work is possible only for a certain range around the disposed place.

In other words, there is a need for a device that may protect the health and life of the people by performing the disinfection function while moving to areas of a multi-use facility used by many people, such as hospitals, public institutions and schools, on behalf of disinfection personnel.

Accordingly, the inventor of this application has come to develop a disinfection robot capable of performing a disinfection work by autonomously moving in a space with the risk of infection and automatically recognizing a disinfection target.

SUMMARY

This disclosure has been designed to solve the above problems, and the present disclosure is directed to providing a disinfection robot, which may perform disinfection by autonomous driving and automatic recognition of disinfection targets so that indirect disinfection based on UV and direct disinfection through disinfectant injection may be performed simultaneously.

A disinfection robot according to an embodiment of the present disclosure is a disinfection robot capable of autonomous driving and recognition of a disinfection target, and the disinfection robot comprises: a recognition unit configured to generate recognition information by recognizing a surrounding environment of the disinfection robot; a movement unit configured to move a position of the disinfection robot; a light source unit configured to emit a light of a predetermined wavelength area for disinfection; an injection unit configured to inject a fluid for disinfection; and a control unit configured to move the disinfection robot through the movement unit based on the recognition information, wherein the control unit is configured to identify a disinfection target from the recognition information and control at least one of the light source unit and the injection unit to perform disinfection to at least one of the surrounding environment of the disinfection robot and the disinfection target.

A disinfection robot according to another embodiment of the present disclosure is a disinfection robot capable of autonomous driving and recognition of a disinfection target, and the disinfection robot comprises: a lower cover unit configured to accommodate a movement unit for moving a position of the disinfection robot; a body unit configured to include a light source for emitting a light of a predetermined wavelength area for disinfection and located on the lower cover unit; a head unit configured to include an injection unit for injecting a fluid for disinfection; a connection unit configured to connect the body unit and the head unit; and at least one recognition unit provided to at least one of the body unit, the head unit and the lower cover unit and configured to generate recognition information by recognizing a surrounding environment of the disinfection robot, wherein at least one of the light source unit and the injection unit is controlled based on the recognition information to perform disinfection to at least one of the surrounding environment of the disinfection robot and the disinfection target.

The disinfection robot according to an embodiment of the present disclosure may perform a disinfection work for a disinfection facility while autonomously driving inside the disinfection facility.

In addition, the disinfection robot according to an embodiment of the present disclosure may automatically identify a disinfection target located inside a disinfection facility to perform intensive disinfection on the identified disinfection target.

In addition, the disinfection robot according to an embodiment of the present disclosure may provide both UV-based indirect disinfection and direct disinfection through disinfectant injection, thereby providing a more effective disinfection work.

DETAILED DESCRIPTION

Hereinafter, a preferred embodiment according to the present disclosure will be described in detail with reference to the accompanying drawings. The following detailed description provided along with the accompanying drawings is intended to describe an exemplary embodiment of the present disclosure, and is not intended to represent the only embodiment in which the present disclosure may be implemented. The following detailed description includes specific details to provide a thorough understanding of the present disclosure. However, one of ordinary skill in the art can recognize that the present disclosure may be practiced without these specific details. Specific terms used in the following description are provided to help understanding of the present disclosure, and these specific terms may be changed into other forms in use within the scope of the technical idea of the present disclosure.

Figure 1:
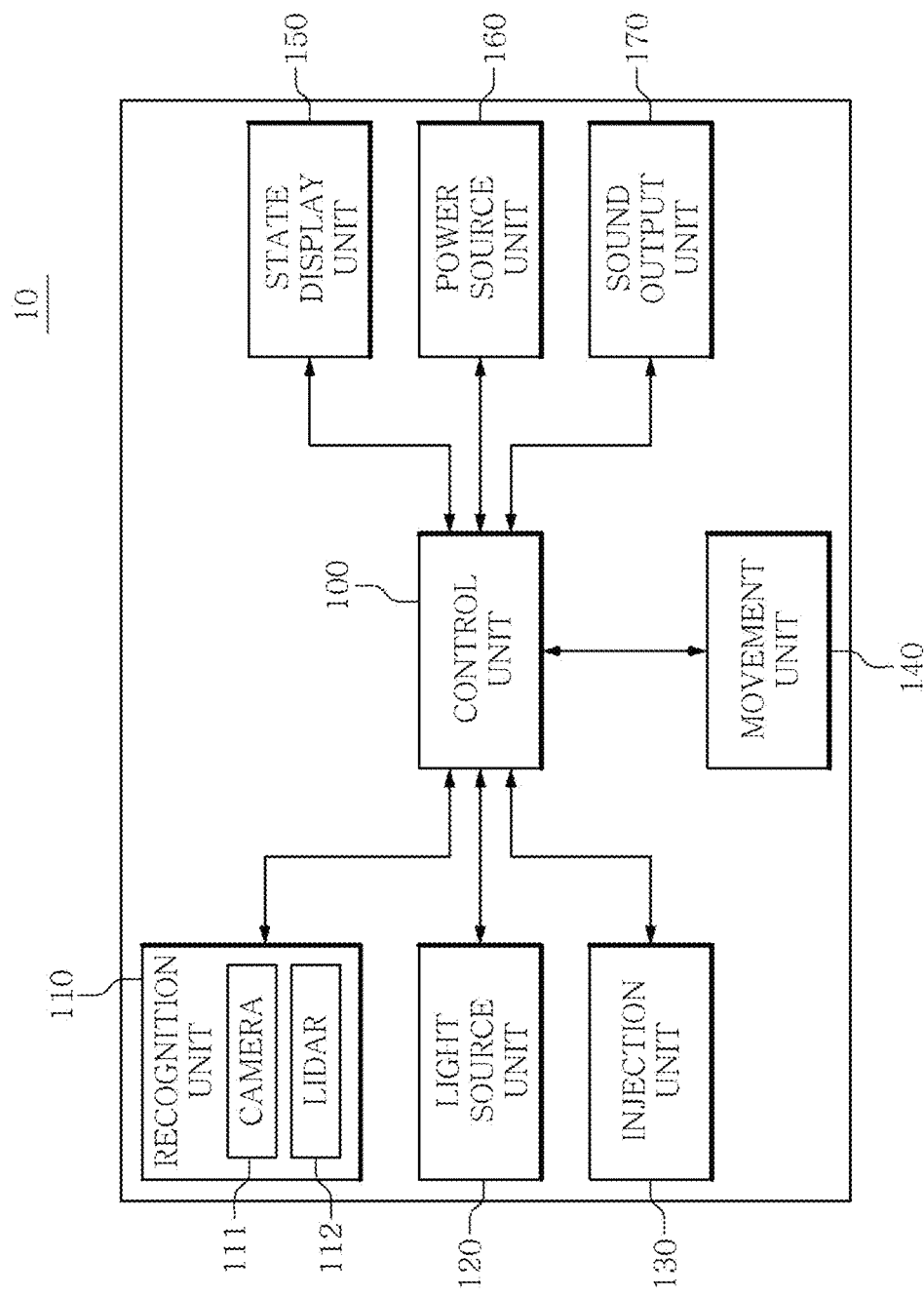
FIG. 1 is a diagram showing a configuration of a disinfection robot according to an embodiment of the present disclosure.

FIG. 1 is a diagram showing a configuration of a disinfection robot according to an embodiment of the present disclosure.

A disinfection robot 10 according to an embodiment of the present disclosure may move in a disinfection space through autonomous driving, and recognize a disinfection target in the disinfection space to perform a disinfection work to the disinfection target. The disinfection robot 10 may simultaneously perform indirect disinfection based on a light source target and direct disinfection through disinfectant injection to a disinfection facility and a disinfection target.

Referring to FIG. 1, the disinfection robot 10 according to an embodiment of the present disclosure includes a control unit 100, a recognition unit 110, a light source unit 120, an injection unit 130, a movement unit 140, a state display unit 150, a power source unit 160 and a sound output unit 170.

The disinfection robot 10 may be entirely hardware, or may be partly hardware and partly software. For example, in this specification, the disinfection robot and each unit included therein may collectively refer to a device for sending and receiving data of a specific format and content through an electronic communication method and software related thereto. In this specification, terms such as "unit", "module", "server", "system", "device" or "terminal" are intended to refer to a combination of hardware and software driven by the hardware. For example, herein, the hardware may be a data processing device including a CPU or another processor. In addition, the software driven by hardware may refer to a process in execution, an object, an executable file, a thread of execution, a program, and the like.

In addition, each module constituting the disinfection robot 10 is not intended to refer to a separate component that is physically distinct. In FIG. 1, the control unit 100, the recognition unit 110, the light source unit 120, the injection unit 130, the movement unit 140, the state display unit 150, the power source unit 160 and the sound output unit 170 are shown as separate blocks separated from each other, but here, the devices constituting the disinfection robot are only functionally classified by actions performed by the corresponding devices. Therefore, depending on an embodiment, the control unit 100, the recognition unit 110, the light source unit 120, the injection unit 130, the movement unit 140, the state display unit 150, the power source unit 160 and the sound output unit 170 are partly or entirely integrated in the same device, one or more units may be implemented as a separate device that is physically separated from other units. In addition, these units may be components that are communicatively connected to each other in a distributed computing environment.

The control unit 100 controls operations of main components of the disinfection robot 10.

The recognition unit 110 generates recognition information by recognizing a surrounding environment of the disinfection robot. The recognition unit 110 may include different types of heterogeneous sensors, and may generate recognition information based on information collected from the heterogeneous sensors. In an embodiment, the recognition unit 110 may include at least one camera 111 for photographing the surrounding environment of the disinfection robot 10 and at least one LIDAR 112. The camera 111 may generate an image signal in real time by photographing the surrounding environment of the disinfection robot 10. The LIDAR 112 emits a signal around the robot to detect the surrounding environment of the disinfection robot, and may generate a sensing signal related to a spatial position of a reflection point by measuring the time of the signal reflected by and returned from the surrounding environment. The sensing signal generated by the LIDAR 112 corresponds to a point cloud composed of a plurality of point information provided from a plurality of reflection points. In an embodiment, the recognition information generated by the recognition unit 110 may include the image signal generated by the camera 111 and the sensing signal generated by the LIDAR 112.

The control unit 100 may control autonomous driving of the disinfection robot based on the recognition information provided by the recognition unit 110. The movement unit 140 may be a component for moving a position of the disinfection robot. In an embodiment, the movement unit 140 may be configured in a wheel manner for easy movement on a flat floor. For example, the movement unit 140 may be configured with an omni wheel or a mecanum wheel to facilitate movement on a flat floor in all directions. However, the configuration of the movement unit 140 is not limited thereto. In some embodiments, the disinfection robot 10 may have a shape similar to a human, and the movement unit 140 may be configured with two legs to implement bipedal walking, which is a moving method of a person. The control unit 100 may move the disinfection robot through the movement unit 140 based on the recognition information.

The control unit 100 may recognize the surrounding environment of the disinfection robot based on the image signal provided by the camera 111 and generate a map of the disinfection facility where the disinfection robot moves. In other words, even if a map of the disinfection facility is not provided in advance, the disinfection robot may perform autonomous driving based on the generated map of the disinfection facility. Here, the disinfection facility refers to a facility where the disinfection robot 10 performs a disinfection work, and may be a multi-use facility used by many people, such as hospitals, public institutions, and schools, without being limited thereto.

The control unit 100 may control autonomous driving of the disinfection robot 10 and a disinfection work of the disinfection robot 10 inside the disinfection facility together. The control unit 100 may control the disinfection robot 10 to perform the disinfection work for the surrounding environment while moving. The control unit 100 may recognize an obstacle included in the surrounding environment by using the sensing signal generated by the LIDAR 112 and move the disinfection robot 10 while avoiding the recognized obstacle. In addition, the control unit 100 may recognize a wall surface of the disinfection facility through the sensing signal and allows the disinfection robot 10 to move along the wall surface so that the disinfection robot 10 keeps a certain distance from the wall to secure a sufficient space for the disinfection work. That is, the control unit 100 may move the disinfection robot 10 by applying the wall following function.

In addition, the control unit 100 may identify a disinfection target included in the surrounding environment based on the recognition information and control a disinfection work for the identified disinfection target. In other words, the control unit 100 may further perform an intensive disinfection work to the identified disinfection target and objects around the identified disinfection target. Specifically, the control unit 100 may identify the disinfection target included in the image signal by analyzing the image signal provided from the camera 111. The disinfection target may be a device or tool used by many people in the disinfection facility. For example, the disinfection target may be buttons in an elevator, a sofa in a break room, a door handle, and so on, which many people use together. The control unit 100 may include a disinfection target analysis model learned to identify a disinfection target from the image signal and may identify a disinfection target by using this disinfection target analysis model. In addition, the control unit 100 may control the disinfection robot 10 to keep a certain distance from the disinfection target through the sensing signal generated by the LIDAR 112. In a state where a distance or space is secured for disinfection, the disinfection robot 10 may effectively perform the disinfection work (direct disinfection and indirect disinfection).

The control unit 100 may perform disinfection to the identified disinfection target by controlling at least one of the light source unit 120 and the injection unit 130. The control unit 100 may operate the light source unit 120 and the injection unit 130 selectively or sequentially in consideration of the characteristics of the identified disinfection target. In addition, the control unit 100 may operate the light source unit 120 and the injection unit 130 at the same time in consideration of the characteristics of the identified disinfection target. That is, the control unit 100 may perform disinfection for at least one of the surrounding environment of the disinfection robot 10 and the disinfection target by controlling at least one of the light source unit 120 and the injection unit 130. For example, the control unit 100 may perform the disinfection work to the inside of the disinfection facility by emitting light from the light source unit 120 while the disinfection robot 10 is moving inside the disinfection facility.

The light source unit 120 may include at least one light source that emits light in a wavelength range for disinfection. For example, the light source unit 120 may include a UV-C light source configured to emit light in a UV-C wavelength area with a high sterilization effect for bacteria and viruses, and may emit light corresponding to a wavelength area of 100-280 nm. However, the present disclosure is not limited thereto, and the light source unit 120 may be configured to change the wavelength range of the emitted light in response to the disinfection target. In other words, the light source unit 120 may be configured to be easily replaced with a light source that outputs a wavelength area suitable for the disinfection target, or may be configured to emit light of several wavelength areas from one light source so as to be controlled to output a specific wavelength according to a command of the control unit 100.

Disinfection may be performed to the surrounding environment of the disinfection robot 10 and the disinfection target by the light emitted from the light source of the light source unit 120. The light source of the light source unit 120 may be disposed to emit light from at least one of a front surface, a rear surface, both side surface, a bottom surface and a top surface of the disinfection robot 10. For example, the light source may be disposed at the front surface, both side surfaces and the rear surface of the disinfection robot 10 to perform a disinfection work to the surrounding environment of the disinfection robot 10 and may also be disposed at the bottom surface of the disinfection robot 10 to perform a disinfection work to the floor on which the disinfection robot 10 moves.

The injection unit 130 may inject a fluid for disinfection (or, a disinfectant). The injection unit 130 may include at least one injection nozzle for injecting the fluid, and the stored fluid may be injected through the injection nozzle according to a control signal from the control unit 100. The disinfectant may be injected to the environment of the disinfection facility of the disinfection robot 10 and the disinfection target through the injection unit 130, and accordingly disinfection may be performed to the surrounding environment and the disinfection target. The fluid may be a disinfectant to sterilize the disinfection target. The fluid may be injected in a liquid state from the injection unit 130. However, the present disclosure is not limited thereto, and the fluid may also be injected in a gaseous state.

Here, if the disinfection robot 10 injects the fluid while moving in one direction, a moving direction of the disinfection robot 10 may be opposite to the direction in which the fluid is injected from the injection unit 130. If the disinfection robot 10 moves in one direction, the injecting direction of the fluid may be another direction that is opposite to the one direction. That is, since the fluid is not directly injected into the disinfection robot 10, the influence of the fluid injected from the injection unit 130 on the disinfection robot 10 may be minimized.

The state display unit 150 may indicate an operation state of the disinfection robot 10. The state display unit 150 displays the change of state of the disinfection robot 10 as a color change, so that the change of state of the disinfection robot 10 may be checked by the naked eye of people located around the disinfection robot 10. The state display unit 150 may be configured with a color changeable LED, without being limited thereto. The state display unit 150 may display different colors for a moving state and a disinfection work state (indirect disinfection or direct disinfection) of the disinfection robot 10. In addition, if an abnormal state occurs in the disinfection robot 10, the state display unit 150 may notify it to the surroundings through the state display unit 150.

The sound output unit 170 operates in response to the state display unit 150, and may notify the state of the disinfection robot 10 to the surrounding environment with a sound. The disinfection robot 10 may provide a guidance speech corresponding to the current operation state to the surroundings through the sound output unit 170. For example, the sound output unit 170 may output a guidance speech corresponding to a notification before disinfection, start and end of fluid (disinfectant) injection, and start and end of light source (UV-C) disinfection.

Here, the control unit 100 of the disinfection robot 10 may recognize a person included in the surrounding environment based on the recognition information. If a person approaches the disinfection robot 10 while the disinfection robot 10 is performing disinfection work, the disinfection robot 10 may provide a guidance speech requesting the recognized person to move away through the sound output unit 170.

The power source unit 160 may provide a power required for operating components of the disinfection robot 10. The power source unit 160 may be configured in the form of a rechargeable battery pack.

In addition, the control unit 100 may be configured to exchange data with a user terminal (not shown) through a communication network. According to the signal transmitted through the user terminal, the control unit 100 may be configured to operate the disinfection robot 10.

The disinfection robot 10 providing the above functions may be accommodated in a housing that configures an appearance of the disinfection robot 10, and the housing may be configured to sufficiently provide the function of every component. Hereinafter, an example of implementing the disinfection robot 10 through the housing will be described with reference to FIGS. 2 to 11. In addition, FIG. 1 and the above descriptions related to FIG. 1 may be referred to for explanation and understanding of the following embodiment.

Figure 2:
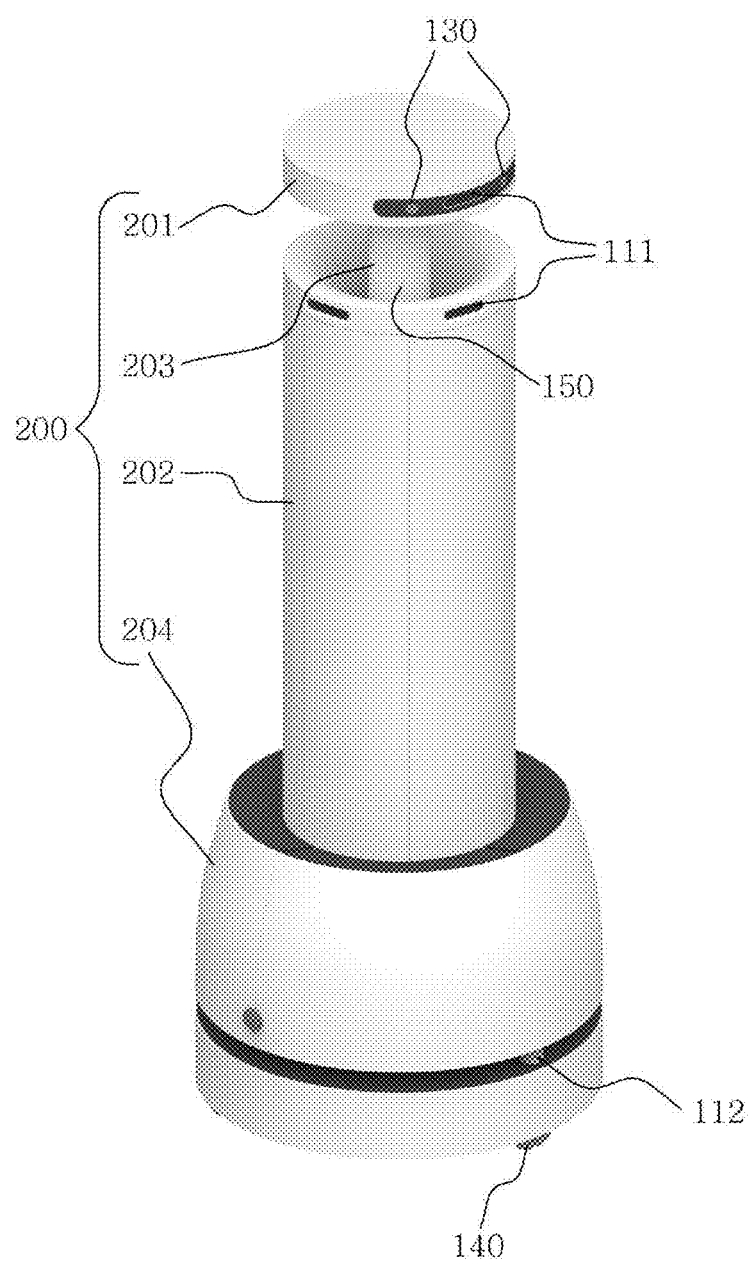
FIG. 2 is a perspective view showing the disinfection robot.
Figure 3:
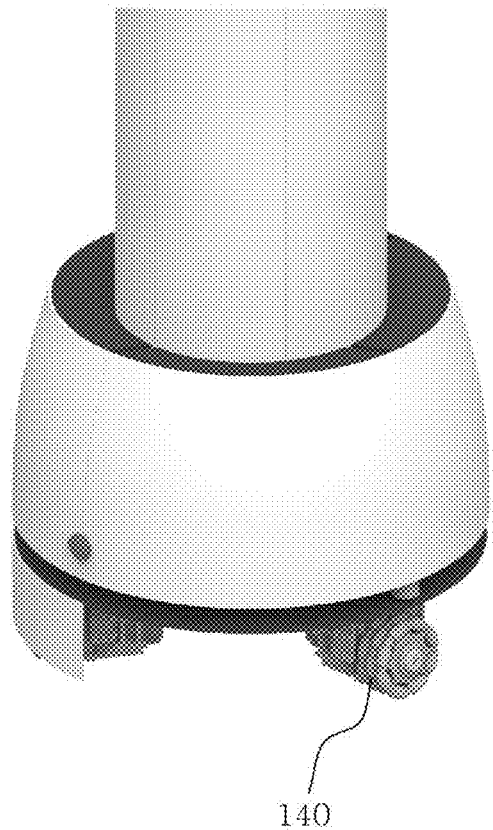
FIG. 3 shows a movement unit accommodated in a lower cover unit.
Figure 7:
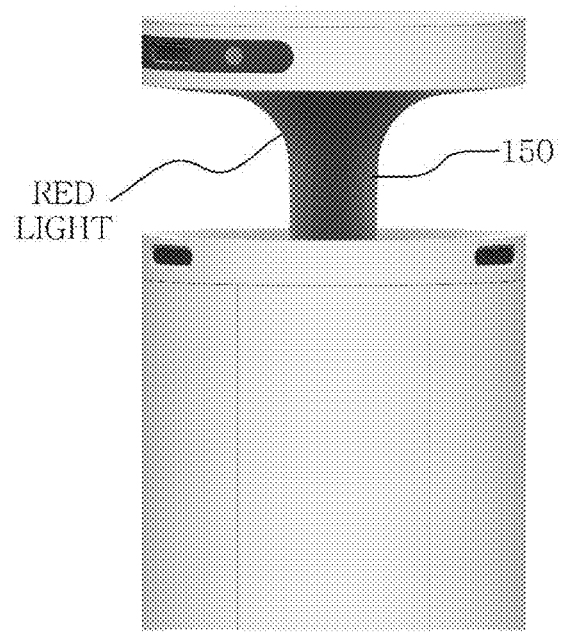
Figure 8:
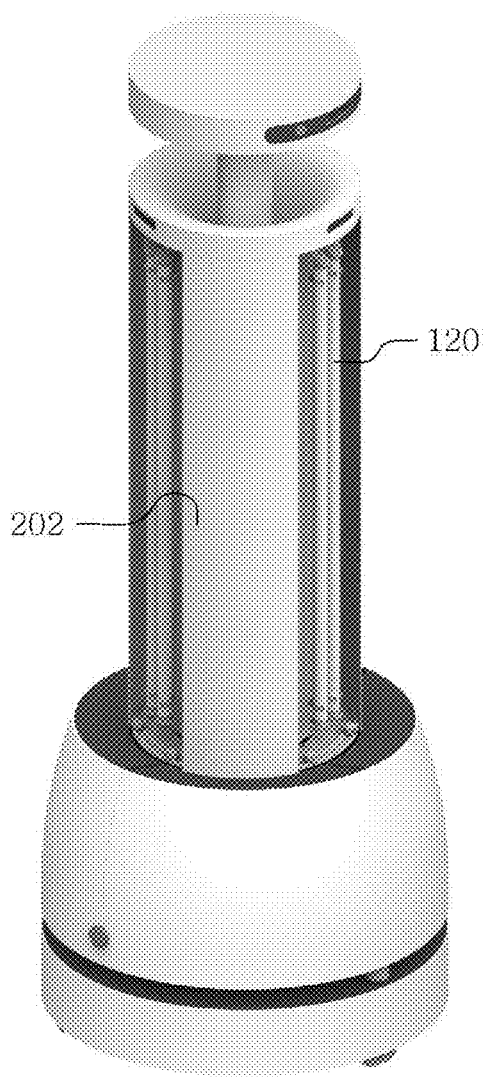
FIG. 8 shows a light source accommodated in a body unit.
Figure 9:
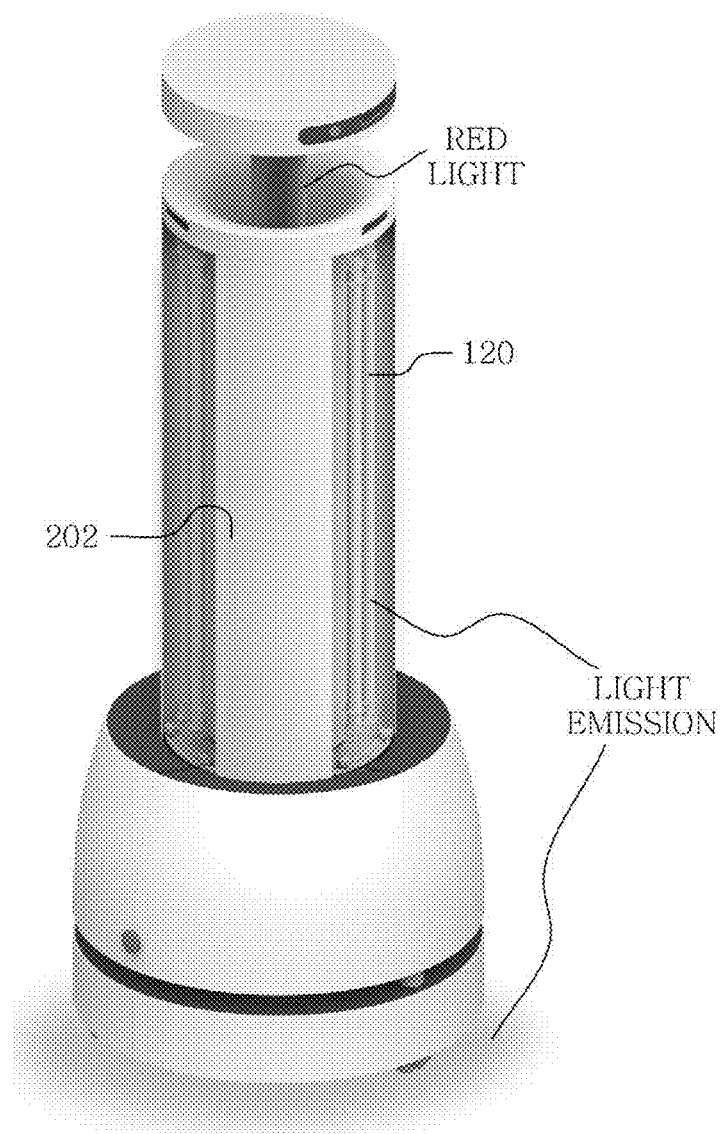
FIG. 9 is an exemplary diagram for illustrating a state where the light source and the state display unit are operated.
Figure 10:
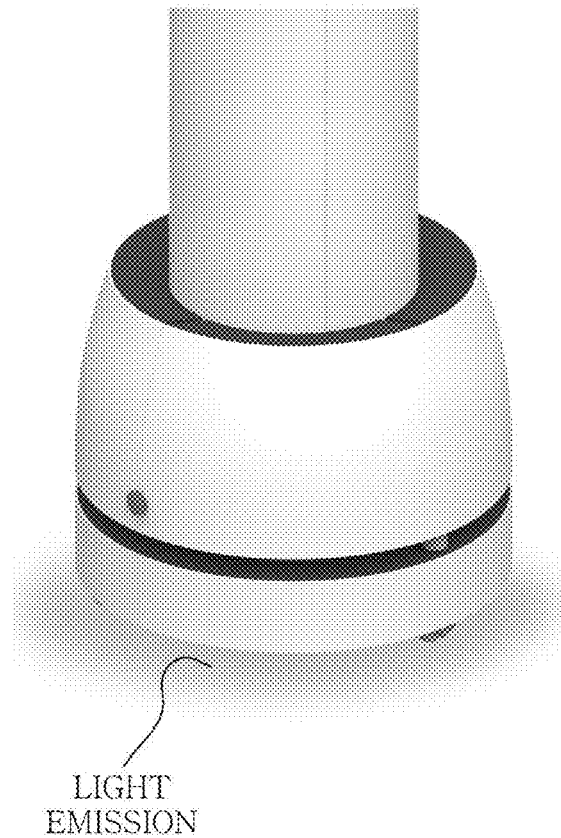
FIG. 10 is an exemplary diagram for illustrating a state where a light source further included in the lower cover unit is operated.

FIGS. 2 to 10 show an appearance of the disinfection robot according to an embodiment of the present disclosure. FIG. 2 is a perspective view showing the disinfection robot. FIG. 3 shows a movement unit accommodated in a lower cover unit. FIGS. 4 to 7 are exemplary diagrams for illustrating a function of a connection unit. FIG. 8 shows a light source accommodated in a body unit, and FIG. 9 is an exemplary diagram for illustrating a state where the light source and the state display unit are operated. FIG. 10 is an exemplary diagram for illustrating a state where a light source further included in the lower cover unit is operated.

Referring to FIG. 2, the disinfection robot 10 is a disinfection robot capable of autonomous driving and recognition of a disinfection target, and the housing 200 configuring the appearance of the disinfection robot 10 includes a head unit 201, a body unit 202, a connection unit 203 and a lower cover unit 204. Here, the housing 200 of the disinfection robot 10 is configured to correspond to a human body and may accommodate main components of the disinfection robot 10. The head unit 201 may correspond to the face of a person, the body unit 202 corresponds to the body of a person, the connection unit 203 corresponds to the neck of a person, and the lower cover unit 204 corresponds to the leg of a person.

The lower cover unit 204 accommodates the movement unit 140 for the movement of the disinfection robot 10. Referring to FIG. 3, the movement unit 140 may be configured with an omni wheel to facilitate movement on a flat floor in all directions, and may be accommodated in the lower cover unit 204 to be minimally exposed to the outside.

The body unit 202 is located on the lower cover unit 204 and may include a light source 120 that emits light of a predetermined wavelength for disinfection.

The connection unit 203 has one end connected to the body unit 202 and the other end connected to the head unit 201 to connect the body unit 202 and the head unit 201. The head unit 201 includes the injection unit 130 that injects a fluid for disinfection. The injection unit 130 is accommodated in the head unit 201, which is an upper portion of the disinfection robot 10, so that the fluid may be injected at a high position. Since the fluid is injected at a high position, the disinfection range may be expanded by the fluid of the disinfection robot 10.

The control unit 100 moves the disinfection robot 10 through the movement unit 140 based on the recognition information, identifies a disinfection target from the recognition information, and controls at least one of the light source 120 and the injection unit 130 to perform disinfection to at least one of the surrounding environment of the disinfection robot 10 and the disinfection target. The power source unit 160 may provide a power required for operating components of the disinfection robot 10. The control unit 100 and the power source unit 160 may be accommodated in the lower cover unit 204, without being limited thereto.

Here, the connection unit 203 may connect the head unit 201 and the body unit 202 to adjust an injecting direction of the injection unit 130 in a state where the disinfection robot is stopped. For example, the connection unit 203 may be connected to the body unit 202 so as to be rotatable along a horizontal plane in a state of being fixed to the head unit 201. If comparing FIGS. 4 and 5, in a state where the disinfection robot is stopped, the head unit 201 and the connection unit 203 are fixed, and the body unit 202 may perform a yaw motion based on the connection unit 203 connected to the body unit 202 to enable rotation along a horizontal plane. According to the yaw motion of the head unit 201, the injecting direction of the injection unit 130 may be changed. However, the connection relationship between the connection unit 203 is not limited thereto, and, in another embodiment, the connection unit 203 may be connected to the head unit 201 so that the head unit 201 may rotate along a horizontal plane in a state where the connection unit 203 is fixed to the body unit 202. The control unit 100 may determine the injecting direction of the injection unit 130 by controlling the yaw motion of the head unit 201 in consideration of at least one of the moving direction of the disinfection robot 10 and the identified disinfection target. For example, the control unit 100 may control the direction of the head unit 201 so that the fluid is injected in a direction opposite to the moving direction of the disinfection robot 10.

In addition, the connection unit 203 may connect the head unit 201 and the body unit 202 so that the injecting angle of the injection unit 130 is adjusted while the disinfection robot is stopped. For example, the connection unit 203 may connect the head unit 201 and the body unit 202 so that the head unit 201 rotates along a vertical plane perpendicular to the horizontal plane in a fixed state with the head unit 201. That is, the connection unit 203 may be connected to the body unit 202 to make a pitch motion corresponding to the movement of the head unit 201 nodding up and down. Comparing FIGS. 4 and 6, when the disinfection robot is stopped, the head unit 201 and the connection unit 203 are connected in a fixed state, and the head unit 201 may make a pitch motion based on the connection unit 203 connected to the body unit 202 to be rotatable along a vertical plane. The injecting angle located at the head unit 201 may be adjusted according to the pitch motion of the head unit 201. If intensive injection to the recognized disinfection target is required, the control unit 100 may adjust the angle of the head unit 201 so as to be closes to the disinfection target. For example, the control unit 100 may intensively inject the fluid to the disinfection target by tilting the head unit 201 toward the disinfection target.

The recognition unit 110 may be located to at least one of the body unit 202, the head unit 201 and the lower cover unit 204 of the disinfection robot 10 to generate recognition information by recognizing the surrounding environment of the disinfection robot. At least one recognition unit 110 may be provided, and the recognition unit 110 may include at least one camera 111 for photographing the surrounding environment of the disinfection robot 10 and at least one LIDAR 112.

Referring to FIG. 2, the LIDAR 112 may be located at a lower portion of the disinfection robot 10 in order to easily recognize an obstacle located on a movement path of the disinfection robot 10, particularly an obstacle located on the floor. That is, the LIDAR 112 may be accommodated in the lower cover unit 204 to more efficiently generate a recognition signal.

The camera 111 may be configured to be located at the upper portion of the disinfection robot 10 to have a wide field of view (FoV). The camera 111 may be provided in plural, and the plurality of cameras 111 may be located at the head unit 201 and the body unit 202, respectively. The camera 111 located at body unit 202 may generate an image signal to make a map of the disinfection facility. The camera 111 may be located to at least the front surface and the rear surface of the body unit 202. However, the present disclosure is not limited thereto, and the camera 111 may also be located at the front surface, the rear surface and the side surfaces of the body unit 202. A map of the disinfection facility may be generated based on the image signal generated by each camera 111.

The camera 111 located at the head unit 201 may generate an image signal to identify a disinfection target located in the surrounding environment of the disinfection robot 10. The control unit 100 may adjust at least one of direction and angle of the head unit 201 at which the camera 111 is installed in order to obtain an additional image signal for identifying the disinfection target identified from the image signal of the camera 111 in order detail in a state where the disinfection robot 10 is located in place.

Figure 4:
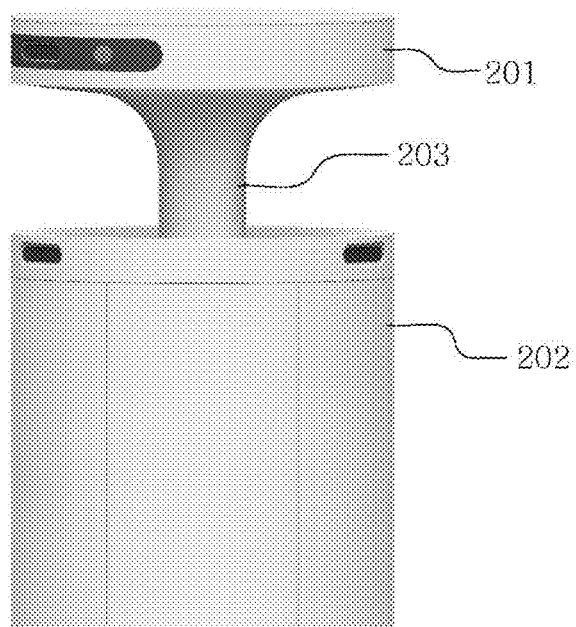
FIGS. 4 to 7 are exemplary diagrams for illustrating a function of a connection unit.
Figure 5:
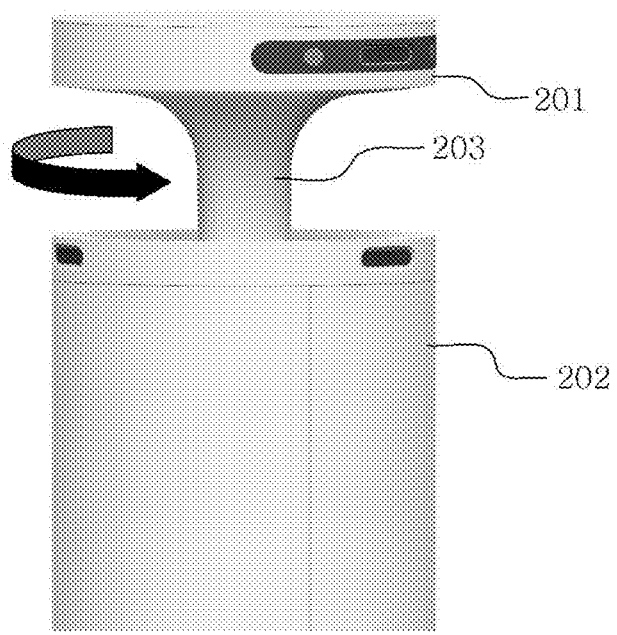
Figure 6:
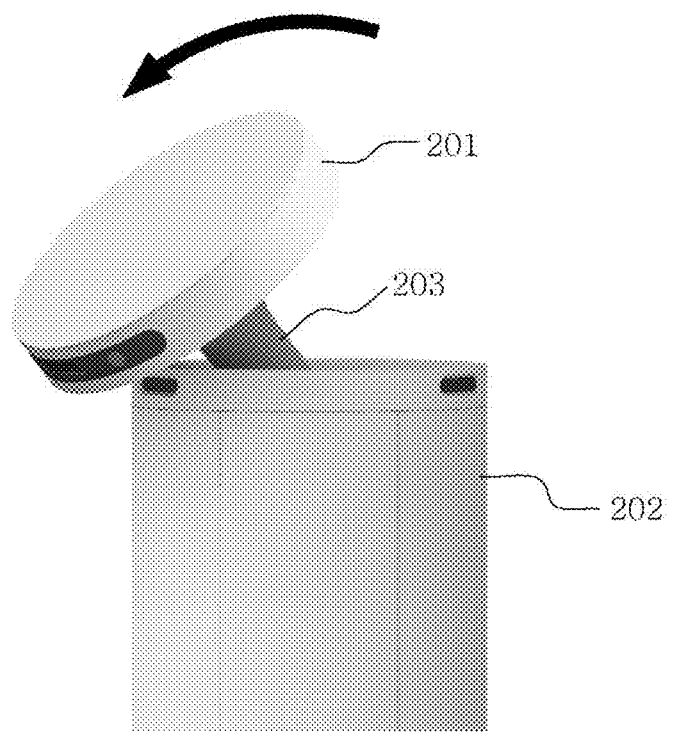

In addition, the disinfection robot 10 may further include a state display unit 150 that displays an operation state of the disinfection robot, and as shown in FIG. 7, the state display unit 150 may be included in the connection unit 203. The state display unit 150 may include an LED configured to display different colors according to the operation state of the disinfection robot. It may be found that the state display unit 150 shown in FIG. 7 is lighted in red to indicate the state where the disinfection robot 10 starts the disinfection work, compared to FIG. 4 showing the state before the disinfection robot 10 operates.

Here, as shown in FIG. 8, the light source 120 may be disposed inside the body unit 202 to correspond to the extending direction of the body unit 202. The light source 120 is configured to have a length corresponding to the length of the body unit 202, and accordingly, the disinfection robot 10 provides a wide range of light emitting areas and enables effective disinfection work. The light source 120 may be disposed to at least one of the front surface, the side surface and the rear surface of the body unit 202, respectively, and may perform the disinfection work to a surrounding environment corresponding to at least one of the front surface, the side surface and the rear surface of the disinfection robot 10.

The light source 120 may be a UV-C light source configured to emit light in a UV-C wavelength area, which has a high sterilizing effect for bacteria and viruses. Since the light in the UV-C wavelength area also has a harmful effect on the human body, the light source 120 is preferably exposed to the outside only during operation. In addition, considering that the light source 120 is made of a glass material, it may be desirable to configure that the light source 120 is selectively exposed to the outside in order to improve durability and prevent damage of the disinfection robot 10. Therefore, only when the disinfection work is performed by the light source 120, the body unit 202 is opened and the light source 120 is exposed to the outside. That is, if the light source 120 is in a non-operation state, the body unit 202 is in a closed state to prevent the light source 120 from being exposed to the outside. If the light source 120 is in an operation state as shown in FIG. 9, the body unit 202 is opened to expose the light source 120 to the outside. Such selective opening and closing of the body unit 202 may be controlled by the control unit 100. In some embodiments, the control unit 100 may recognize a person included in the surrounding environment based on the recognition information, and if the person approaches the disinfection robot 10 while the disinfection robot 10 is performing the disinfection work through the light source 120, the body unit 202 may be closed to prevent the person from being exposed to the light of the light source 120.

The disinfection robot 10 may further include a light source 120 accommodated in the lower cover unit 204 to perform disinfection to the floor on which the disinfection robot 10 moves. Referring to FIGS. 9 and 10, if the light source 120 is in an operation state, it may be found that the body unit 202 is opened to expose the light source 120 to the outside, and also the light emitted from the light source for performing disinfection to the floor is emitted through the lower portion of the lower cover unit 204. That is, the disinfection robot 10 may further perform the disinfection work to the floor through the light source 120 that emits light toward the floor.

Although the present disclosure has been described above with reference to the embodiments, the present disclosure should not be construed as being limited by these embodiments or drawings, and it should be understood that the present disclosure can be modified and changed in various ways by those skilled in the art without departing from the scope and idea of the present disclosure defined in the appended claims.

The invention claimed is:

1. A disinfection robot capable of autonomous driving and recognition of a disinfection target, comprising:
   at least one processor; and
   at least one memory storing instructions executable by the at least one processor;
   wherein the instructions, when executed by the at least one processor, cause the disinfection robot to:
   generate recognition information by recognizing a surrounding environment of the disinfection robot;
   move a position of the disinfection robot;
   emit a light of a predetermined wavelength area from a light source accommodated in a body of the disinfection robot for disinfection;
   inject a fluid for disinfection in a direction opposite to a moving direction of the disinfection robot when the robot moves in one direction;
   move the disinfection robot based on the recognition information;
   identify a disinfection target from the recognition information and control at least one of the light source and an injecting direction of the fluid to perform disinfection to at least one of the surrounding environment of the disinfection robot and the disinfection target;
   provide a guidance speech requesting a recognized person to move away through a speaker of the disinfection robot when the disinfection robot recognizes the person based on the recognition information during the disinfection;
   based on the disinfection robot recognizing the person, close the body to prevent the person being exposed to the light of the light source; and
   operate the light source and inject the fluid for disinfection selectively or sequentially in consideration of characteristics of the disinfection target, or operate the light source and inject the fluid at a same time in consideration of the characteristics of the disinfection target.

2. The disinfection robot according to claim 1,
wherein the instructions, when executed by the at least one processor, cause the disinfection robot to:
generate an image signal by photographing the surrounding environment of the disinfection robot; and
cause at least one LIDAR to generate a sensing signal obtained by sensing the surrounding environment of the disinfection robot, and
wherein the recognition information includes the image signal and the sensing signal.

3. The disinfection robot according to claim 2,
wherein the instructions, when executed by the at least one processor, cause the disinfection robot to:
generate a map of a disinfection facility where the disinfection robot moves, based on the image signal provided from the camera, and
recognize a wall surface of the disinfection facility based on the sensing signal and move the disinfection robot along the wall surface while keeping a predetermined distance from the recognized wall surface.

4. The disinfection robot according to claim 1, wherein the instructions, when executed by the at least one processor, cause the disinfection robot to:
display an operation state of the disinfection robot.

5. A disinfection robot capable of autonomous driving and recognition of a disinfection target, comprising:
a lower cover configured to accommodate one or more elements for moving a position of the disinfection robot;
a body configured to include a light source for emitting a light of a predetermined wavelength area for disinfection and located on the lower cover;
a head configured to inject a fluid for disinfection in a direction opposite to a moving direction of the disinfection robot when the robot moves in one direction;
a connector configured to connect the body and the head; and
at least one processor; and
at least one memory storing instructions executable by the at least one processor;
wherein the instructions, when executed by the at least one processor, cause the disinfection robot to:
generate recognition information by recognizing a surrounding environment of the disinfection robot,
provide a guidance speech requesting a person to move away through a speaker of the disinfection robot when the disinfection robot recognizes the person based on recognition information during the disinfection, and
operate the light source and inject the fluid for disinfection selectively or sequentially in consideration of characteristics of the disinfection target, or operate the light source and inject the fluid at a same time in consideration of the characteristics of the disinfection target,
wherein at least one of the light source and injection direction of the fluid is controlled based on the recognition information to perform disinfection to at least one of the surrounding environment of the disinfection robot and the disinfection target, and
wherein control of the light source based on the recognition information includes closing the body to prevent the person being exposed to the light of the light source.

6. The disinfection robot according to claim 5,
wherein the body has a shape extending in one direction, and the light source is disposed inside the body to correspond to the extending direction of the body, and
wherein the body is opened to expose the light source to the outside when the light source is in an operation state.

7. The disinfection robot according to claim 5,
wherein the disinfection robot includes at least one LIDAR located at the lower cover, and cameras respectively located at the body and the head,
wherein the cameras generate an image signal by photographing the surrounding environment of the disinfection robot, and the LIDAR generates a sensing signal obtained by sensing the surrounding environment of the disinfection robot, and
wherein the recognition information includes the image signal and the sensing signal.

8. The disinfection robot according to claim 5,
wherein the connector is configured to include a state display configured to display an operation state of the disinfection robot.

9. The disinfection robot according to claim 5,
wherein the connector is configured to connect the head and the body so that an injecting direction of the fluid is adjusted in a state where the disinfection robot stops.

10. The disinfection robot according to claim 5,
wherein the connector is configured to connect the head and the body so that an injecting angle of the fluid is adjusted in a state where the disinfection robot stops.

11. The disinfection robot according to claim 5,
wherein the light source is accommodated in the lower cover to perform disinfection to a floor on which the disinfection robot moves.

* * * * *